United States Patent [19]

Langer, Jr.

[11] 4,434,312
[45] * Feb. 28, 1984

[54] PREPARATION OF LINEAR OLEFIN PRODUCTS

[75] Inventor: Arthur W. Langer, Jr., Watchung, N.J.

[73] Assignee: Exxon Research and Engineering Co., Florham Park, N.J.

[*] Notice: The portion of the term of this patent subsequent to Apr. 29, 1986 has been disclaimed.

[21] Appl. No.: 222,008

[22] Filed: Jan. 2, 1981

Related U.S. Application Data

[63] Continuation-in-part of Ser. No. 882,946, Mar. 2, 1978, Pat. No. 4,396,788, which is a continuation of Ser. No. 232,618, Mar. 7, 1972, abandoned, which is a continuation-in-part of Ser. No. 783,699, Dec. 13, 1968, Pat. No. 3,662,021, which is a continuation-in-part of Ser. No. 562,089, Jul. 1, 1966, abandoned, which is a continuation-in-part of Ser. No. 428,836, Jan. 28, 1965, abandoned, which is a continuation-in-part of Ser. No. 55,845, Sep. 8, 1960, Pat. No. 3,168,588.

[51] Int. Cl.³ .............................................. C07C 2/22
[52] U.S. Cl. ................................... 585/523; 585/524
[58] Field of Search ................................. 585/523, 524

[56] References Cited

U.S. PATENT DOCUMENTS

3,637,897 1/1972 Cull et al. ............................ 585/524
3,660,518 5/1972 Cull et al. ............................ 585/524
3,862,257 1/1975 Buben et al. ........................ 585/523

FOREIGN PATENT DOCUMENTS

1375842 11/1974 United Kingdom ................ 585/523

OTHER PUBLICATIONS

Longi et al., La Chimicae l'Industria, vol. 55, No. 3, Mar. 1973.

Primary Examiner—Paul M. Coughlan, Jr.
Attorney, Agent, or Firm—Richard E. Nanfeldt

[57] ABSTRACT

A process for preparing alpha olefin waxes comprising polymerizing an ethylene containing gas in the presence of a hydrocarbon-soluble catalyst comprising a zirconium compound, a dialkyl aluminum halide and a monoalkyl aluminum dihalide in specified ratios in the presence of a diluent at 75°–200° C. and maintaining the mole ratio of ethylene to total olefin reaction product above 0.8 so as to produce a waxy product containing at least 90 mole % linear olefins of which greater than 50 wt % are $C_{20+}$ waxes.

8 Claims, No Drawings

PREPARATION OF LINEAR OLEFIN PRODUCTS

CROSS-REFERENCE TO RELATED APPLICATIONS

This application is a continuation-in-part of Ser. No. 882,946, filed Mar. 2, 1978 (now U.S. Pat. No. 4,396,788), which is a Rule 60 continuation application of Ser. No. 232,618, filed Mar. 7, 1972 (now abandoned), which is a C.I.P. of Ser. No. 783,699, filed Dec. 13, 1968 (now U.S. Pat. No. 3,662,021), which is a C.I.P. of Ser. No. 562,089, filed July 1, 1966 (now abandoned) which is a C.I.P. of Ser. No. 428,836, filed Jan. 28, 1965 (now abandoned), which is a C.I.P. of Ser. No. 55,845, filed Sept. 8, 1960 (now U.S. Pat. No. 3,168,588).

FIELD OF THE INVENTION

A process for preparing alpha olefin waxes comprising polymerizing an ethylene containing gas in the presence of a hydrocarbon-soluble catalyst comprising a zirconium compound, a dialkyl aluminum halide and a monoalkyl aluminum dihalide in specified ratios in the presence of a diluent at 100°–200° C. and maintaining the mole ratio of ethylene to total olefin reaction product above 0.8 so as to produce a waxy product containing at least 90 mole % linear olefins of which greater than 50 wt. % are $C_{20+}$ waxes.

PRIOR ART

It has been shown in the prior art (U.S. Pat. Nos. 2,993,942 and 2,907,805) that hydrocarbon lubricating oils having a molecular weight in the range of 80 to 2000 could be prepared by polymerizing ethylene with controlled catalyst, diluents and under controlled temperatures. The catalyst consisted of a transition metal halide and a halogenated aluminum alkyl compound. It has also been found that increased oil yields, catalyst reactivity, and improved molecular weight control could be obtained by the addition of a minor amount of a lower alkanol, as a catalyst modifier to the reaction system. Both the modified and unmodified systems described above resulted, under the conditions in the reaction, in the production of major portions of olefins other than linear alpha olefin products, particularly Type II (RCH=CHR),

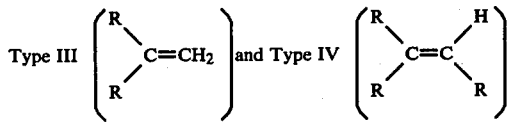

olefins.

It has now been discovered that the polymerization of ethylene under controlled conditions to produce linear olefinic waxes can be made selective for linear alpha olefins by preferably terminating the reaction by the addition of an agent or agents to kill the activity of the catalyst and prevent deleterious side reactions. It has been found that the termination of the reaction by adding conventional catalyst killing agents, e.g. alcohol or water, results in a product other than one comprising at least 90 mole % linear alpha olefins. The process of this invention preferably includes the termination of the ethylene polymerization reaction by the addition of specific agents under specific conditions. The ethylene polymerization reaction comprises a sequence of critical reaction variables comprising, inter alia, a mole ratio of ethylene to product, use of a particular soluble catalyst, ethylene pressure, and product olefin concentration.

SUMMARY OF THE INVENTION

In accordance with this invention, therefore, an improved process for preparing linear olefins, particularly linear alpha olefins, is provided which comprises polymerizing ethylene or an ethylene containing gas in the presence of a substantially soluble catalyst comprising the reaction product of a transition metal halide, the transition metal being selected from the group consisting of reducible heavy metals of Groups IVB to VIB and VIII with an aluminum alkyl compound such that the ultimate formula of the aluminum alkyl compound is $AlR_nX_{3-n}$, wherein n is less than 2, R is a hydrocarbyl radical, and X is a halogen, conducting the polymerization reaction in presence of a suitable diluent, at temperatures below about 75° C. and ethylene pressures above about 50 psia, maintaining the mole ratio of ethylene to olefin reaction product above about 0.8 throughout the reaction, and killing catalyst activity after at least about 5 wt. %, based on diluent, of product olefin has formed by adding an agent or agents to kill the polymerization activity of the catalyst and preventing or inhibiting deleterious side reactions. In an embodiment of this invention a polymerization killing agent is added and another agent, designed to prevent or inhibit side reactions, e.g., isomerization, is added either before, after or simultaneously with the polymerization killing agent. In a preferred embodiment of this invention a single agent can be added to the reaction mixture to accomplish both results, i.e., kill polymerization activity and inhibit deleterious side reactions. In yet another preferred embodiment, the polymerization killing agent is added to the reaction mixture prior to the removal of the ethylene from the reaction mixture. Generally, however, the agent or agents added to the reaction mixture are added under relatively critical conditions.

The reaction can be terminated either by removing the ethylene containing gas thereby stopping the polymerizations or, by adding the polymerization catalyst killing agent, thereby stopping the polymerization activity of the catalyst.

While not wishing to be bound by any particular theory, it is believed that the catalysts employed herein as ethylene polymerization catalysts tend also to promote the copolymerization of the product olefins formed by the reaction. Now since the object of this invention is to produce and maintain a product comprising at least 90 mole % linear olefins, it is obvious that copolymerization of the reaction product will lead to increased formation of branched products at the expense of linear products. Consequently, the reaction must be terminated at a suitable point where an economically feasible product yield has been obtained but prior to the occurrence of copolymerization to the extent that it reduces product purity to a level below about 90 mole % linear olefins. While generally conventional polymerization killing agents can be added to the reaction mixture to terminate the polymerization activity of the catalyst, e.g., water, alcohols, acids, etc., such agents tend to protonate the catalyst and turn it into a strongly acidic Friedel-Crafts catalyst. A Friedel-Crafts catalyst in the reaction mixture, however, promotes isomerizations, alkylations, carbonium ion polymerizations, etc., which are deleterious in that such side reactions reduce the linearity of the reaction product. Consequently, it is often-times necessary to add an additional agent, i.e., a base, to the reaction mixture to neutralize the Friedel-Crafts activity of the catalyst.

Generally, catalyst activity may be killed before or after the ethylene is removed from the reaction mixture. When the catalytic activity is killed after ethylene removal the polymerization killing agent must be added within about one minute after ethylene removal. This is a critical variable in the preservation of the linear olefin reaction product. Thus, as previously mentioned, the polymerization catalyst also promotes copolymerization of the product olefin. However, copolymerization is inhibited due to the relatively high mole ratio of ethylene to product olefin maintained throughout the reaction. (This ratio is maintained by the high ethylene pressure, i.e., above about 50 psia ethylene, in the reaction mixture which promotes ethylene polymerization activity rather than copolymerization.) When the ethylene has been removed the selectivity to ethylene polymerization is lost and copolymerization will be promoted. In order to prevent copolymerization from destroying the linear product it is critical that the polymerization activity of the catalyst be killed within about one minute of ethylene removal. After killing the polymerization activity with a conventional agent, the Friedel-Crafts activity must be neutralized, also within a critical period. Thus, side reactions due to the presence of an acidic catalyst can also destroy the linear reaction product. The base, or neutralizing agent, must then be added within about one minute after the polymerization activity is killed.

Of course, this invention contemplates the addition of the base prior to the addition of the polymerization killing agent. Nevertheless, polymerization activity must be killed within about one minute of ethylene removal. Thus, if the base is added one minute after ethylene removal, the polymerization killing agent must be added simultaneously. However, the base may be added within about two minutes after ethylene removal if the polymerization killing agent is first added about one minute after ethylene removal.

The foregoing critical relationships hold where the reaction is terminated at ambient temperatures, i.e., room temperatures of about 18°–25° C., and above. It will be obvious to those skilled in the art that if the temperature of the reaction mixture is reduced, i.e., taken below room temperature, after the polymerization activity is killed, addition of the base can be delayed somewhat. Of course, the lower the temperature of the reaction mixture, the longer base addition can be delayed. Using the very general rule that reaction rate doubles or halves with each 10° C. change in temperature, a rough guide can be established and the period during which the base must be added (to prevent undue isomerizations, alkylations, etc.) can be readily found by simple experimentation.

Thus, the general rule is that the polymerization activity of the catalyst be killed within about one minute after termination of the reaction. It is preferred, however, to add the polymerization killing agent prior to the termination of the reaction, i.e., before the ethylene is flashed off, a point which is obviously within the general period just stated. This procedure eliminates observance of the critical period when the reaction is terminated prior to killing polymerization activity. Additionally, the critical period for base addition is also obviated since the reaction mixture will be auto refrigerated due to flashing the ethylene, e.g., the temperature can be reduced to below −10° C. by auto refrigeration. Furthermore, at reduced temperatures the catalyst can be washed out thereby eliminating the acid function and obviating the need for a neutralizing agent.

Some typical polymerization killing agents are water; alcohols, both mono and poly hydroxylic, cyclic and acyclic, aliphatic and aromatic; carboxylic acids, phenols, etc. The organic compounds which can be used are those having from 1 to 15 carbon atoms, the lower carbon number inexpensive compounds being preferred. Thus alcohols and acids having from 1 to 8 carbons are preferred, with 1 to 4 carbons being most preferred. Examples of the most preferred killing agents include water, methanol, ethanol, isopropanol, t-butanol, and ethylene glycol.

Bases that can be employed to neutralize Friedel-Crafts activity can be any base that will effectively neutralize this acid function. Generally, such bases can be broadly characterized as Lewis bases. Such materials which can be used in the practice of this invention include caustics such as alkali metal and alkaline earth metal hydroxides, alkoxides, aryloxides and carbonates, ammonium hydroxide and quaternary ammonium bases and organic bases such as organic nitrogen compounds, e.g., ammonia, amines and cyclic nitrogen bases, and ethers, etc. As specific examples, there can be named lithium hydroxide, sodium hydroxide, sodium methoxide, sodium 2,6-di-t-butyl-4 methyl phenoxide, potassium carbonate, magnesium hydroxide, calcium carbonate, tetramethyl-ammonium hydroxide, $C_1$–$C_{10}$ aliphatic amines, e.g., ethylamine, methylamine and aniline, p-toluidine, ammonia, heterocyclic nitrogen compounds, e.g., pyridine, and tetrahydrofuran. These bases may be used alone, in mixtures or dissolved in solvents such as water, alcohols, glycols, etc. The preferred bases are sodium hydroxide or ammonia dissolved in water or alcohols. Although larger amounts may be used, it is desirable to use 0.5 to 2 moles of base per atom of halogen in the catalyst, preferably about stoichiometric amounts. It is obvious that a base such as sodium hydroxide dissolved in water or alcohols serves to kill polymerization activity simultaneously with neutralization. Lewis bases kill polymerization activity by complexing more strongly than alpha olefins with the transition metal site. On the other hand, protonic agents kill polymerization activity by destroying the metal-carbon bonds of the catalyst. Thus, a base is needed in addition to the protonic agents to neutralize the Friedel-Crafts activity of the catalyst residues, whereas a base such as triethylamine or sodium hydroxide inactivates both types of catalyst activity.

Compounds which contain both protonic and Lewis base functional groups are most highly preferred since they are capable of killing both types of catalyst activity with a single quenching agent. Further advantages for these bifunctional compounds are that they are soluble in the oligomer solution, they are effective in amounts less than stoichiometric based on the catalyst components, and the quenched catalyst products are soluble in the oligomer solution. Representative, non-limiting examples include hydroxyethers, hydroxyamines, carboxyethers, carboxyamines, and the like, such as glycol monoethers, aminoalcohols, hydroxyacids and aminoacids. Specific examples include ethylene glycol monomethyl ether, diethylene glycol monomethyl ether, ethoxyethanol, 3-propoxypropanol, 2-dimethylaminoethanol, hydroxyacetic acid, beta-hydroxypropionic acid, glycine and higher natural and unnatural aminoacids, N, N-dialkylaminoacids, mono-, di-, and triethanolamines, and the like.

The catalyst which can be used is a complex reaction product which is substantially soluble in the polymerization system and is obtained by partially reacting a reducible, heavy transition metal halide or a transition metal compound of selected Group IVB to VIB to VIB or VIII metal with an aluminum alkyl compound such that the ultimate formula of the aluminum alkyl compound is $AIR_nX_{3-n}$, wherein n is less than 2, R is alkyl, cycloalkyl or aralkyl, preferably containing 1 to 20 carbon atoms, for example, methyl, ethyl, isobutyl, cyclohexyl, benzyl, etc., and X is Cl or Br or I. While most transition metal halides are suitable components of the catalyst complex, when the desired product is the branched chain olefins of the prior art, it has been found that compounds such as $VCl_4$ and $FeCl_3$ are unsuitable for the preparation of linear alpha-olefins. The preferred transition metal catalyst component is a titanium compound having a valency of 3 or 4, preferably 4, and may be represented by the formula $TiX_aA_b$, wherein a=3 or 4, b=0 or 1 and a+b=3 or 4, X=Cl or Br and A is Cl or Br or an anion derived from a protonic compound such as an alcohol (R'OH) or a carboxylic acid (R'COOH). The R' of the protonic compound may be an alkyl, aryl, aralkyl or cycloalkyl group. The $TiX_aA_b$ component may be made in situ by reacting $TiX_4$ with the protonic compound. Thus, the preferred transition metal component of this invention may be selected from the group $TiX_4$, $TiX_3OR'$ and $TiX_3OOCR'$. Typical examples of such compounds are $TiCl_4$, $TiBr_4$, $TiX_3OC_2H_5$, and $TiX_3OOCCH_3$, $TiX_2(OC_2H_5)_2$, $TiX(OC_2H_5)_3$, and $Ti(OC_2H_5)_4$.

The transition metal component may also be a halide, an alkoxide, an aryloxide or a carboxylate derivative of tetravalent zirconium or hafnium having the general formulas $MX_n(OR')_{4-n}$ and $MX_n(OOCR')_{4-n}$, where M=Zr or Hf, X=Cl or Br, n=0 to 4 and R' may be an alkyl, aryl, aralkyl or cycloalkyl group. When these components are reacted with the excess aluminum alkyl chlorides, exchange of ligands take place involving halide, alkyl, alkoxide and carboxylate groups. In addition to exchange of aluminum alkyl groups with transition metal ligands, the aluminum halide groups can also exchange with alkoxy and carboxyl groups on the transition metal compound. These compounds may also be made in situ by reacting the more readily available $MX_4$ with R'OH or R'COOH. The alcohols may be unsaturated as in the case where they are the enol forms of carbonyl compounds such as acetyl acetone. Typical examples include $ZrCl_4$, $ZrBr_4$, $ZrCl(OEt)_3$, $ZrCl_2(OC_{10}H_{21})_2$, $ZrBr_3OBu$, $Zr(OPr)_4$, $Zr(OBu)_4$, $ZrCl_2(O\phi)_2$, $ZrCl_2(OOCC_9H_{19})_2$, $ZrCl(OOC\phi)_3$, $ZrCl_3OOCCH_3$, $ZrCl_2$ glycoxide, Zr acetyl acetonate, $ZrCl_3(O$-cyclohexyl$)$, $HfCl_4$, $HfBr_4$, $Hf(OBu)_4$, etc.

The hydrocarbon soluble Zirconium compounds containing alkoxide, aryloxide, carboxylate or enolate groups preformed or made in situ are preferred for making waxes. The most preferred catalysts for a wax process contain 2-4 alkyl groups.

Catalyst polymerization activity can be enhanced and product molecular weight may be controlled by the addition of small amounts of alcohol which react in situ with the transition metal halide compounds to form transition metal alkoxides such as $TiCl(OBu)_3$, $TiCl_2(OBu)_2$, $TiCl_3OBu$, or $Ti(OBu)_4$, depending upon the amount of alcohol added to the transition metal halide compound. The alcohols which can be used in the practice of this invention are those having from 1 to 15 carbon atoms, preferably those having from 1 to 8 carbons, and most preferably those alcohols having 1 to 4 carbon atoms. Thus, the alcohols that can be used include methanol, ethanol, n-propanol, isopropanol, n-butanol, secbutanol, tertiary butanol, isobutanol and all of the $C_5$ and $C_6$ alcohols. $C_3$ to $C_6$ diols in which the hydroxy groups are not attached to adjacent carbon atoms are also useful. Especially preferred and desirable are: tertiary butanol, secondary butanol, iso- or n-butanol, and isopropanol. These alkanols are utilized in a minor amount, i.e. so that the ratio of ROH/R (based on aluminum alkyl) after alkylation or reduction of the transition metal is not greater than 0.5.

As set forth above, it is preferred that the aluminum alkyl catalyst after reaction with the transition metal halide have the formula $AIR_nX_{3-n}$. The molar ratio of alkyl aluminum halide to the transition metal halide is not critical to this invention as long as the $AIR_nX_{3-n}$ reaction product has the proper formula. The ratio may be 0.1/1 to 150/1 or more. Catalyst concentration is normally in the range of 0.1 to 10 grams per liter of diluent.

One embodiment of the instant application relates to a process for preparing a reaction product comprising at least about 90 mole % linear alpha-olefins having a number average molecular weight varying from about 70 to about 700 which comprises polymerizing an ethylene containing gas in the presence of a substantially soluble catalyst, said catalyst formed from the reaction product of a Group IV-B metal halide, an aluminum alkyl compound and a prototonic compound such that the ultimate formula of the aluminum alkyl compound is $AIR_nX_{3-n}$ where R is selected from the group consisting of an alkyl, aralkyl and cycloalkyl, X is selected from the group consisting of chlorine, bromide and iodine, and n is less than 2, such prototonic compound being selected from the group comprising R'OH and R'COOH wherein R' of the prototonic compound may be an alkyl, aryl, aralkyl or cycloalkyl group in an amount sufficient so that the ratio of either R'OH or R'COOH to R (based on aluminum alkyl) after alkylation of the metal halide, is not greater than 0.5.

Ethylene is unique in the instant invention in that other olefins do not respond to give linear alphaolefins. Therefore, it is desirable to use essentially pure ethylene or mixtures of ethylene with inert gases as the feed for the process of this invention. Ethylene feeds containing minor amounts of other olefins may be used provided that the extent of copolymerization does not decrease product linearity below 90%.

Polymerization diluent is not a critical feature of this invention. The usable diluents are aromatic hydrocarbon and haloaromatic solvents as well as aliphatics and naphthenics. Less preferred solvents are halogenated aliphatic compounds which, while capable of being employed in the process of preparing linear alpha-olefins, require the utilization of higher pressures to achieve average molecular weights of the same order as the preferred solvents. The preferred diluents include halogenated aromatics such as chlorobenzene, dichlorobenzene, chlorotoluene, etc., and aromatics such as benzene, toluene, xylene, tetrahydronaphthalene, etc., aliphatics such as pentane, heptane, iso-octane, etc., and naphthenes such as cyclohexane, methylcyclohexane, decahydronaphthalene, etc. The suitable halogenated aliphatic diluents include methyl chloride, ethyl chloride, dichloromethane, etc. Mixtures of these diluents may be used. Also, mixtures of the above types with aliphatic or naphthenic solvents may be used. The diluent or diluent mixture may be used to control the product molecular weight distribution to obtain maximum selectivity to the desired olefin products. Recycle olefin fractions above, about $C_6$, preferably above about $C_{16}$ but less than about $C_{30}$ may also be used as diluents.

The prior art obtained highly branched olefins (60%) when using the closely related catalyst and diluent systems at pressures of 7 to 30 psig., e.g., British Pat. No. 874,577. Ethylene pressures above 50 psia are essential for making linear olefins in high selectivities. Although some variations are permitted depending upon the catalyst composition, diluent and temperature, the preferred pressures are above about 80 to 100 psia in order to produce commercially attractive yields (at least above 5 weight % and preferably above 10 weight % olefins in the reactor effluent) of linear alpha-olefins having a purity greater than about 90 mole %. The most preferred range is above 100 psia ethylene pressure. At very high ethylene pressures the process may become uneconomical becuase of the equipment requirements and ethylene recycle. Nevertheless, higher pressures tend to increase the selectivity of the reaction to linear alpha-olefins and increases selectivity to $C_{20}$ and waxes also.

The ratio of moles of ethylene to the moles of products throughout the reaction and insured by the ethylene pressures referred to above, must be above about 0.8 in order to effect the selective synthesis of linear olefins from ethylene and inhibit copolymerization effects. The preferred ratio of ethylene to products is above about 2.0. The upper limit of the mole ratio of ethylene to product is not critical. The mole ratio of ethylene to product must be above 0.8 or the product formed contains more than 10% branched chain olefins at product concentrations required to obtain commercially attractive yields.

The catalyst of this invention enables the process for making linear alpha-olefins to be carried out at temperatures below $+75°$ C., preferably between about $-30°$ C. and about $+50°$ C. The selection of a particular temperature will permit control of the average number molecular weight of the product. With zirconium and hafnium catalysts, temperatures as high as about 200° C. can be used without making excessive amounts of polyethylene. However, the high temperatures cause product isomerization and require higher ethylene pressures to prevent copolymerization which make them less attractive. The preferred temperatures to obtain greater than 50 wt. % $C_{20+}$ waxes with zirconium catalysts are below about 150° C. and most preferably, below about 125° C.

In a process for making greater than 50 wt. % $C_{20+}$ waxes, the ratios of $AlR_2X'/Zr$ and $AlRX_2/ZR$ are critical for molecular weight control. The molar ratio of $AlR_2X'/Zr$ should be in the range 0.5-2, preferably about 1, and the ratio of $AlRX_2/ZrY_4$ should be 2-6, preferably about 3-4, the ratio of $AlRX_2/ZrY_3X$ should be 2-4, preferably about 3 and the ratio of $AlRX_2/ZrY_2X_2$ should be 0-3, preferably about 1-2, wherein $Y=OR^1$, $OOCR^1$ or enolate groups as defined previously, and $X=Cl$ or Br, and $x^1=F$, Cl, Br or I. Most peferably, $Y=OR'$ and $X=Cl$. Improved activity and molecular weight control is obtained by premixing the $AlR_2X'$ and the Zr compound in a relatively concentrated solution in the substantial absence of the $AlRX_2$ component. This solution is quite stable and may be stored for weeks without significant decomposition, whereas the total catalyst mixture decomposes on standing to the heterogeneous Ziegler-type catalyst which produces high molecular weight polyethylene rather than olefin waxes. The two catalyst solutions may be mixed just prior to use or they may be fed separately to the reactor. More rapid pretreatment may be done in concentrated solutions at 0°-150° C. for 1-60 minutes or in dilute solutions at elevated temperatures.

In a process for making waxes with zirconium catalysts, the reaction temperatures is in the range 75° to 200° C., preferably about 100° to 180° C. and most preferably about 120° to 150° C. Temperature above about 100° C. is needed to maintain wax solubility and prevent precipitation on the cooling surfaces. Temperatures above about 120° C. are preferred in order to maintain solubility of the heavy ends of the wax distribution, as well as any polyethylene by-product. Catalyst concentration is normally in the range of about 0.001 to about 2 g/liter of diluent, preferably about 0.01 to 0.5, depending upon the residence time and the desired product concentration and purity.

Reaction times are not particularly critical when operating under the preferred conditions and they will normally be in the range of 1 minute to 5 hours to obtain product concentrations greater than 5% by weight in the diluent. The process may be carried out in batch or continuous operation. However, high product purity and high concentration are achieved most easily in batch reactions or in continuous systems operating under essentially plug flow conditions. A reactor may consist of a long pipe through which the diluent and catalyst flow with ethylene being introduced at many points along the pipe to maintain the desired ethylene concentration. In such a system monomer concentration need not be constant but may be controlled differently in different sections of the reactor to achieve the best balance of activity, molecular weight and product purity. Stirred tank reactors may be operated in series to approach plug flow.

After the catalyst has been effectively neutralized, the residues may be removed from the products in any conventional way, such as washing with water or aqueous caustic, dilute aqueous acid, adsorption, ion exchange resins, etc. If the catalyst has been neutralized according to this invention, the products may be distilled directly from the catalyst residues without decreasing product purity. However, it is preferred to remove the residues before distillation in order to minimize deposits in the distillation towers.

Based on the teachings of this invention to destroy both polymerization and Friedel-Crafts activity to permit isolation of greater than 90% pure linear alpha-olefins, it is clearly within the scope of the invention to accomplish the same results by alternatives such as rapid solvent extraction or solid adsorption techniques, particularly if these are used before all of the ethylene has been flashed. However, such techniques are generally less effective than the preferred neutralization procedure.

The following examples are submitted in order to more particularly point out applicant's invention but are not to be construed as limitations upon the scope of the instant invention as described in the appended claims.

EXAMPLE 1

A series of runs were made to determine the effect of ethylene pressure on product linearity. All were carried out at −20° C. using 500 ml of either chlorobenzene or xylene diluent. The proportions of catalyst components were maintained constant, although total catalyst concentration was varied by a factor of four. The $TiCl_4$ in 400 ml diluent was added to the reactor under dry nitrogen and cooled to −20° C. The t-butyl alcohol and $AlEt_2Cl$ were mixed 5 minutes in 100 ml diluent before adding the $AlEtCl_2$. The latter was added to the reactor and the total mixture allowed to react 15 minutes at −20° C. High purity ethylene was obtained by passing commercial C.P. ethylene over copper oxide at 205° C. to remove oxygen and then through 3A molecular sieves to remove water. It was stored in a one-gallon reservoir at 1000 psig. After the catalyst pretreatment, the reactor contents were subjected to high speed stirring. Ethylene was added as necessary to maintain pressure and the temperature was kept at −20° C. by circulating coolant through coils around the reactor.

The results are summarized in Table I. After killing the catalyst with about 25 to 50 ml methanol containing NaOH, the product was water-washed twice and dried over $K_2CO_3$. The products were analyzed quantitatively for olefin types by infrared, and the split between linear and branched products was determined by quantitative gas chromatography on a sample of total reactor product. Using a four-foot column of silicone gum rubber and temperature programming, it was possible to obtain the yield of each product up to $C_{36}H_{72}$. Product linearity is expressed as mole % in the $C_{12-20}$ fraction. It was compared on the $C_{12-20}$ cuts because this was the most accurate analysis considering volatility losses from $C_{4-10}$ and G. C. resultion of the branched and linear olefins above $C_{20}$. The linearity of the total product is much higher than that shown for the $C_{12-20}$ fraction because in all pressure runs the $C_{4-10}$ fraction is essentially 100% linear, and it is a major protion of the total product.

As shown in Table I, the selectivity to linear alpha-olefins increases sharply above about 50 psia and becomes greater than 90% above about 100 psia. At still higher ethylene pressures, selectivity rapidly approaches 100% in the $C_{12-20}$ fraction. Excellent results were obtained with either chlorobenzene or xylene diluent. In addition to the effect on olefin linearity, ethylene pressure may be used together with catalyst composition, solvent polarity and polymerization temperature to control the product molecular weight. As shown in Table I for chlorobenzene diluent, the number average molecular weight increased from 98.8 at atmospheric pressure to 147 at 500 psia.

xylene was pretreated 30 minutes at 15° C., cooled to 0° C. and ethylene added rapidly. Polymerization was carried out two hours at 0° C. and 520 psia ethylene pressure. Samples of the total reactor product were taken hourly and analyzed as in Example 1.

In taking the reactor samples, the ethylene is allowed to flash off at atmospheric pressure, thereby refrigerating the sample. The first hour sample (10 ml) was allowed to stand 15 minutes before killing the catalyst with 1 ml of 1 M NaOH in methanol. The second hour sample (18 ml) was pressured from the reactor directly into a vessel containing the 1 ml of 1 M NaOH in order to kill the catalyst immediately. The amount of NaOH was taken to be approximately equivalent to the chloride content of the catalyst in the sample.

Alkylation took place so extensively in the first hour sample that it was impossible to do the usual analysis. Product concentration was estimated to be about 30 to 40 weight %. No linear alpha-olefins were indicated by infra-red analysis. The product was predominantly alkylated xylene.

The second hour sample was 96.9% linear alphaolefins despite the fact that product concentration was much higher (53.6 weight %). By analogy with all other experiments, the first hour sample should have had the highest linearity; in this case, an estimated 98 to 99% of the catalyst had been destroyed immediately after flashing ethylene.

This example illustrates that high purity olefins can only be obtained by rapid destruction of the catalyst activity after flashing ethylene.

EXAMPLE 3

A catalyst solution was prepared by reacting 12 mmoles $AlEt_2Cl$ and 2 mmoles t-butanol in 95 ml chlorobenzene for 5 minutes, then adding 12 mmoles $AlEtCl_2$. 400 ml chlorobenzene containing 2 mmoles $TiCl_4$ was charged to the reactor, cooled to −20° C., the aluminum alkyl solution was added, and the catalyst was pretreated 15 minutes at −20° C. Ethylene was charged to 155 psia and polymerization was continued one hour at 150 to 160 psia and −20° C.

The total reactor product was flashed into 100 ml methanol without any base present. After filtering off 4.8 grams wax, the filtrate was water-washed, dried over $K_2CO_3$ and distilled using a 15 plate Oldershaw column at 20/1 reflux ratio. Infrared analysis of the $C_4$-$C_8$ cut gave only 80% linear alpha-olefins and 20% internal olefins (Type II-trans). Since some Type II-cis olefins would have been produced simultaneously by

TABLE I

| Run | mmoles[a] A/B/C/D | Diluent | Hours | psia $C_2H_4$ | g. Product/ g. $TiCl_4$/Hr. | $\overline{M}_n$[c] | % Linear Olefins in $C_{12-20}$ |
|---|---|---|---|---|---|---|---|
| 3 | 12/12/2/2 | $C_6H_5Cl$ | 1 | 15[b] | 45 | 98.8 | 67 |
| 4 | 12/12/2/2 | $C_6H_5Cl$ | 1 | 55 | 95 | 100.5 | 70 |
| 5 | 12/12/2/2 | Xylene | 1 | 140 | 105 | 121.4 | 98 |
| 6 | 6/6/1/1 | $C_6H_5Cl$ | 1 | 165 | 147 | 112.6 | 97 |
| 7 | 3/3/0.5/0.5 | $C_6H_5Cl$ | 2 | 250 | 74 | 121.3 | 99 |
| 8 | 12/12/2/2 | Xylene | 1 | 250 | 97 | 140.0 | 100 |
| 9 | 12/12/2/2 | $C_6H_5Cl$ | 0.5 | 500 | 126 | 147.0 | 100 |

A B C D
[a]Catalyst: $AlEt_2Cl/AlEtCl_2/TiCl_4$/t-BuOH
[b]Gaseous ethylene bubbled continuously through diluent at atmospheric pressure
[c]Number average molecular weight of total olefin product.

EXAMPLE 2

A catalyst solution containing 1.5 mmoles $AlEt_2Cl$ 3.0 mmoles $AlEtCl_2$ and 3.0 mmoles $TiCl_4$ in 250 ml isomerization, the linear alpha-olefin purity was considerably less than 80%.

Experiments in which the products were flashed into methanol plus NaOH gave over 98% pure linear alpha-olefins. In the infrared analyses of these samples, the Type II-trans absorption at 10.3μ was barely discernible.

This example illustrates that rapid equenching of the catalyst polymerization activity is not sufficient to obtain high purity alpha-olefins. In the absence of a base, double bond isomerization occurs to produce the less desirable internal olefins. It shows that it is critical to destroy the Friedel-Crafts activity of the catalyst as well as the polymerization activity. Besides double bond isomerization, residual catalyst Friedel-Crafts activity could also cause alkylation and cationic polymerizations which would further decrease the alpha-olefin purity.

With high polymers any residual polymerization or Friedel-Crafts activity has a negligible effect, if any, on product properties. In a process for making linear alpha-olfins, however, it is critical to destroy or neutralize both types of catalyst activity.

EXAMPLE 4

Following the procedure of Example 3 but terminating the polymerization with 10 ml methanol plus 10 ml 6 N NH$_4$OH prevented isomerization and preserved the alpha-olefin purity.

EXAMPLE 5

A series of runs were made to determine the effect of quenching various catalyst compositions. The reaction conditions are set forth in Table II. In each run the reaction was quenched with a mixture of methanol and NaOH. It is to be seen from Table II that the instant process resulted in a highly linear product.

TABLE II

| Run | 1 | 2 | 3 | 4 |
|---|---|---|---|---|
| AlEtCl$_2$, mmoles | 5 | 2 | 5 | 0.5 |
| AlCl$_3$, mmoles | 0 | 0 | 0.2 | 0 |
| TiCl$_4$, mmoles | 1 | 1 | 0.05 | 1 |

TABLE II-continued

| Run | 1 | 2 | 3 | 4 |
|---|---|---|---|---|
| $\overline{M}_n$ | 113 | 128 | 114 | 116 |

(a) Assuming mono-alkylation of TiCl$_4$
(b) Excluding 10-20% losses during work-up
(c) Determined on C$_{12-20}$ fraction

EXAMPLE 6

A catalyst solution was prepared by mixing 0.1 mmole ZrCl$_4$ and 0.2 mmole phenol in 40 ml chlorobenzene for 5 minutes at 50° C., then adding 0.4 mmole Al$_2$Et$_3$Cl$_3$ and pretreating 15 minutes at 60° C. The solution was rinsed into a pressure catalyst bomb with an additional 10 ml chlorobenzene and pressured with ethylene into the reactor containing 150 ml chlorobenzene and 890 psia C$_2$H$_4$ at 70° C. The temperature and pressure were immediately raised to 75° C. and 1015 psia ethylene pressure and maintained for 30 minutes.

G.C. samples were flashed into 1 M NaOH in methanol, n-heptane was added and the solutions were washed with aqueous K$_2$CO$_3$ solution, separated and dried over solid K$_2$CO$_3$. Analyses were carried out using a 15 ft. column of SE-30 (2% on Chromosorb G) and temperature programming to 340 C. The yield of olefins between C$_4$ and about C$_{40}$ after 15 minutes was 48 g and after 30 minutes it was 90 g. Linear alpha olefin purity in the C$_{12-20}$ fraction was 99+%. Extraction of the wax with boiling n-heptane yielded less than 0.1 g insoluble product.

EXAMPLE 7

The procedure of Example 6 was followed except that n-butanol was used in place of phenol and it was mixed with either the ZrCl$_4$ or the ethyl aluminum sesquichloride for 5 minutes at 25° C. before adding the second catalyst component and pretreating. In Runs 1 and 2 of Table III, no alcohol was added. Variations in catalyst composition, catalyst pretreatment and reaction conditions are given in the Table.

TABLE III

| Run | mmoles A/B/C/D(a) | Diluent | Catalyst Pretreat, OC/min. | Temp, °C. | Time, Min. | g. Olefins/ g. Catalyst(b) | $\overline{M}_n$ | % Linear Olefins in C$_{12}$-C$_{20}$ |
|---|---|---|---|---|---|---|---|---|
| 1 | 0.8/0.8/0.1/0 | C$_6$H$_5$Cl | 60/30 | 75 | 30 | 262 | 93 | 99+ |
| 2 | 0.2/0.2/0.05/0 | C$_6$H$_5$Cl | 80/30 | 100 | 30 | 1295 | 111 | 98 |
| 3 | 0.4/0.4/0.1/0.4 | C$_6$H$_5$Cl | 50/15 | 75 | 60 | 1090 | 148 | 98 |
| 4 | 0.4/0.4/0.1/0.4(c) | C$_6$H$_5$Cl | 90/15 | 75 | 30 | 385 | 158 | 99+ |
| 5 | 0.2/0.2/0.05/0.2 | C$_6$H$_5$Cl | 50/15 | 125 | 30 | 1275 | 154 | 95 |
| 6 | 0.4/0.4/0.1/0.4 | n-C$_7$H$_{16}$ | 50/15 | 75 | 30 | 262 | 140 | 99+ |

(a) Catalyst: AlEt$_2$Cl/AlEtCl$_2$/ZrCl$_4$/n-BuOH.
(b) Excluding the n-butanol.
(c) The n-butanol was reacted first with the Al$_2$Et$_3$Cl$_3$ rather than with ZrCl$_4$.

| Solvent | Xylene | Xylene | C$_6$H$_5$Cl | C$_6$H$_5$Cl |
|---|---|---|---|---|
| ml | 125 | 125 | 250 | 250 |
| Pretreat, °C./min. | 25/60 | 50/30 | 50/30 | 50/30 |
| Al/Ti Mole Ratio | 5 | 2 | 104 | 0.5 |
| Et/Al Ratio(a) | 0.8 | 0.5 | 0.95 | 0 |
| Polymerization | | | | |
| Temp. °C. | 15 | 50 | 50 | 50 |
| C$_2$H$_4$, psia | 400 | 400 | 200 | 400 |
| Time, Hrs. | 1 | 1 | 3 | 0.5 |
| Results | | | | |
| Yield, g.(b) | 132 | 92 | 23 | 51 |
| Linearity, Mole %(c) | 91.5 | 91.2 | 95.2 | 94.3 |

In all runs catalyst activity was excellent. The purity of the linear alpha olefins in the C$_{12-20}$ fraction ranged from 95% to nearly 100%. Total product molecular weight ranged from 93 to 158, illustrating the control of product distribution. At $\overline{M}_n=93$, selectivity to C$_{4-10}$ is 76.8% whereas at the higher molecular weights ($\overline{M}_n=140-158$), one obtains the highest selectivity to C$_{12-18}$ detergent range olefins.

No significant amount of polyethylene was obtained in any of these experiments.

EXAMPLE 8

The procedure of Example 7 was followed except that zirconium propoxide and zirconium dipropoxy dichloride were preformed rather than being made in situ by reacting $ZrCl_4$ with propanol. Variations in catalyst composition, pretreatment and reaction conditions are summarized in Table IV.

TABLE IV

| Run | mmoles A/B/C[a] | Diluent | Catalyst Pretreat, °C./min. | Temp. °C. | Time, Min. | g. Olefins/ g. Catalyst | $\overline{M}_n$ | % Linear Olefins in $C_{12-20}$ |
|---|---|---|---|---|---|---|---|---|
| 1 | 0.2/0/0.2 | n-$C_7H_{16}$ | 50/15 | 50 | 30 | 0 | — | — |
| 2 | 0.2/0.6/0.1 | n-$C_7H_{16}$ | 80/5 | 50 | 30 | 572 | 188 | 99+ |
| 3 | 0.9/0.9/0.2 | $C_6H_5Cl$ | 50/15 | 75–170[c] | 15 | 652 | 141 | 95 |
| 4 | 0/0.8/0.2[b] | $C_6H_5Cl$ | 60/15 | 50 | 30 | 417 | 172 | 99+ |

[a]A/B/C = $AlEt_2Cl/AlEtCl_2/Zr(OPr)_4$
[b]$ZrCl_2(OPr)_2$ was used in place of the tetraalkoxide.
[c]Lost temperature control allowed temperature to rise to about 170° C. momentarily. Most of the run was at 80° C.

Run 1 used equimolar amounts of $AlEt_2Cl$ and $Zr(OPr)_4$ and was completely inactive, whereas Run 2 used 8:1 Al:Zr mole ratio and was very active. This illustrates that preformed zirconium alkoxides require an excess of aluminum alkyl halide just as was found for the in situ preparation using the alcohols. In either case, the ratio of ROH (or RO groups on the Group IVB metal)/R (based on aluminum alkyl) after alkylation of the transition metal is perferably less than about 0.5.

Run 3 produced a small amount of polyethylene, presumably because of the excessively high reaction temperature reached momentarily. Based on this result and those in Example 7, the maximum desirable reaction temperature is about 150° C. for the zirconium catalysts. Product purity drops at the higher temperatures due to copolymerization and isomerization of the alpha olefins so that the preferred reaction temperature for making high purity linear alpha olefins is below 125° C., most preferably below about 75° C.

Run 4 shows that performed zirconium alkoxy chlorides are as effective as those formed in situ from the alcohols. Having demonstrated the utility of $ZrX_4$, $ZrX_2(OR)_2$ and $Zr(OR)_4$, it is clear that other mixed alkoxy halides will also be useful (for example, $ZrCl_3OR$, $ZrCl(OR)_3$, etc.).

EXAMPLE 9

The procedure of Example 6 was followed except that 0.2 mmole neodecanoic acid (Enjay Chemical Co.) was used in place of phenol. Neodecanoic acid is a mixture of $C_{10}$ acids having three alkyl substituents on the alpha carbon ($R_1R_2R_3CCOOH$). The mole ratio of 2 acids per $ZrCl_4$ yields the dichloro dicarboxylate, $ZrCl_2(OOOR)_2$.

After 30 minutes at 75° C. and 1015 psia ethylene pressure, the olefin yield was 68 g. and the purity was 99+%.

EXAMPLE 10

The procedure of Example 6 was followed except that 0.4 mmole acetylacetone was used in place of phenol and the $ZrCl_4$-acetylacetone reaction product was pretreated 15 minutes at 50° C. with 0.8 mmole $Al_2Et_3Cl_3$. The alcohol form (enol) of acetylacetone reacts with the catalyst in the same manner as saturated alcohols. The product (91 g) was 99% pure linear alpha olefins.

EXAMPLE 11

The procedure of Example 6 was followed except that 0.3 mmole benzoic acid was used in place of phenol, yielding a clear, colorless solution with the 0.1 mmole $ZrCl_4$. Addition of 0.6 mmole $Al_2Et_3Cl_3$ and pretreatment for 15 minutes at 50° C. produced a clear, very light yellow solution. After 30 minutes oligomerization at 75° C. and 1015 psia ethylene pressure, a high yield of high purity linear alpha olefins was obtained.

EXAMPLE 12

The procedure of Example 1, Run 4, was followed except that 6 mmoles t-BuOH was used (3 t-BuOH/$TiCl_4$ mole ratio) instead of 2 mmoles and the ethylene pressure was 165–180 psia. Polymerization rate was 163 g/g $TiCl_4$/hr and $M_n$=103. High purity linear alpha olefin reaction product was degraded to 90% purity by an unsatisfactory catalyst quench.

EXAMPLE 13

The procedure of Example 1, Run 6, was followed except that the t-BuOH was reacted with the $TiCl_4$ instead of the aluminum alkyl at 10° C. for 30 min. and ethylene pressure was 145 psia instead of 160 psia. The yield of olefin product was 17 g, $\overline{M}_n$=113 and $C_{12-20}$ purity was >99%.

EXAMPLE 14

The procedure of Example 8, Run 2, was followed except for changes in catalyst proportions, pretreat conditions, diluent and reaction conditions as summarized in Table V. Although reaction conditions varied somewhat, the most significant variable affecting selectivity to wax is the molar ratio of $R_2AlCl/RAlCl_2/Zr(OR)_4$. Runs A–E show that high ratios of either $R_2AlCl$ (Run A) or of the alkyl aluminum sesquichloride (equal moles of $R_2AlCl$ and $RAlCl_2$) (Runs B–E) produce low selectivities to $C_{20+}$ wax. No activity was obtained at a 1 to 1 ratio of ethyl aluminum sesquichloride to $ZR(OPr)_4$ (Run F), 1 to 1 $Et_2AlCl$ to $Zr(OPr)_4$ (Run G), or 3 to 1 ratio of $EtAlCl_2$ to $Zr(OPr)_4$ (Run H).

TABLE V

| Run | Mole Ratio A/B/C[a] | A + C Pretreat [Zr]/°C./min[b] | Diluent, 300 ml | Oligomerization °C. | MPa | Min | g. Product/ g. Zr(OPr) 4/hr | % Purity[c] | % Selectivity to $C_{20+}$ Wax |
|---|---|---|---|---|---|---|---|---|---|
| A | 6/1/1 | 0.05/25°/1 day | Toluene | 120 | 5.6 | 15 | 24,100 | 97.0 | 19 |
| B | 16/16/1 | None | Toluene | 115 | 7 | 30 | 22,400 | 98.6 | 13 |

TABLE V-continued

| Run | Mole Ratio A/B/C[a] | A + C Pretreat [Zr]/°C./min[b] | Diluent, 300 ml | Oligomerization °C. | MPa | Min | g. Product/ g. Zr(OPr) 4/hr | % Purity[c] | % Selectivity to $C_{20+}$ Wax |
|---|---|---|---|---|---|---|---|---|---|
| C | 4/4/1 | 0.05/25°/1 day | Toluene | 120 | 5.6 | 15 | 39,600 | 97.5 | 44 |
| D | 3/3/1 | 0.05/25°/2 days | Toluene | 120 | 5.6 | 15 | 31,200 | 98.8 | 45 |
| E | 2/2/1 | None | Toluene | 115 | 7 | 30 | 2,740 | 99+ | 46 |
| F | 1/1/1 | 2.5/75°/15 | Xylene | 75 | 7 | 30 | 0 | — | — |
| G | 1/0/1 | 8/100°/30 | Toluene | 120 | 7 | 30 | 0 | — | — |
| H | 0/3/1 | 2.5/75°/15 | Xylene | 75 | 7 | 30 | 0 | — | — |
| I | 2/4/1 | 5/80°/15 | Toluene | 110 | 7 | 30 | 18,480 | 97.0 | 55 |
| J | 1/3.5/1 | 5/100°/30 | Toluene | 125 | 7 | 30 | 8,850 | 99+ | 55 |
| K | 1/4/1 | 0.05/25°/2 days | Toluene | 120 | 5.6 | 15 | 19,000 | 99+ | 62 |
| L | 1/4/1 | 4/100°/30 | Toluene | 110 | 7 | 30 | 19,500 | 99+ | 64 |
| M | 1/5/1 | None | Toluene | 115 | 7 | 30 | 17,400 | 96.6 | 70 |
| N | 1/8/1 | 0.05/25°/2 days | Toluene | 120 | 5.6 | 15 | 19,000 | 99+ | 43 |

[a]A/B/C = $Et_2AlCl/EtAlCl_2/Zr(OPr)_4$.
[b][Zr] = Molarity of $Zr(OPr)_4$.
[c]Wt % Linear alpha olefins in $C_{12-20}$ fraction.

However, when the ratio of $R_2AlCl$ to $Zr(OR)_4$ was 2 or less and the ratio of $RAlCl_2$ to $Zr(OR)_4$ was 3.5–5 to 1 (Runs I–M) the catalysts gave greater than 50 wt % selectivity to $C_{20+}$ wax at high catalyst activity and high purity. At a higher ratio of $RAlCl_2$ to $Zr(OR)_4$ (8 to 1), selectivity to wax again decreases to low values. Therefore, the ratios required for a wax process (greater than about 50% selectivity to $C_{20+}$ wax) are very critical and are the following: about 0.5/1 to 2/1 $R_2AlX/Zr(OR)_4$, preferably about 1/1; about 2/1 to 6/1 $RAlX_2/Zr(OR)_4$, preferably about 3/1 to 5/1, and most preferably about 4/1.

EXAMPLE 15

The procedure of Example 14, Run K, was followed except that the catalyst pretreat time was studied. Reaction conditions were 350 ml toluene, 119° C., 7 MPa $C_2H_4$ for 30 minutes using 0.1 mmole $Et_2AlCl$, 0.4 mmole $EtAlCl_2$ and 0.1 mmole $Zr(OPr)_4$. In all runs the alpha olefin purity was 99+%.

Selectivity to wax increased with increasing pretreat time at 25° C. (Runs O–T) and with increasing pretreat temperature (Run U). The 1 to 1 $Et_2AlCl$ to $Zr(OPr)_4$ solution is a stable, soluble catalyst for more than 25 days at 25° C., and is conveniently prepared and stored in large batches as long as the ratio does not substantially exceed 1 to 1. Aging the total catalyst solution (also containing the $EtAlCl_2$) results in the formation of heterogeneous Ziegler catalyst which produces polyethylene instead of alpha olefins.

Catalyst pretreatment is not essential to obtain high selectivity to wax if the optimum catalyst ratios are used, but it can be used to increase the selectivity significantly. Thus, together with the advantages of preparing and storing a large homogeneous catalyst stock solution, it is preferred to use this particular catalyst pretreatment in a wax process.

TABLE VI

| Run | A/B/C mmoles | A + C Pretreat [Zr]/°C./hrs. | g. Product/ g. Zr(OPr)4/ hr. | % Selectivity to $C_{20+}$ Wax |
|---|---|---|---|---|
| O | 0.1/0.4/0.1 | 0.05/25/2 | 9,100 | 58 |
| P | 0.1/0.4/0.1 | 0.05/25/4 | 8,060 | 61 |
| Q | 0.1/0.4/0.1 | 0.05/25/5 | 8,800 | 62 |
| R | 0.1/0.4/0.1 | 0.05/25/6 | 8,620 | 63 |
| S[a] | 0.05/0.2/0.05 | 20/25/24 | 15,000 | 63 |
| T[b] | 0.05/0.2/0.05 | 20/25/25 days | 25,500 | 67 |
| U[b] | 0.08/0.32/0.08 | 4/100/0.5 | 19,500 | 64 |

[a]Run temperature = 115° C.
[b]Run temperature = 110° C.

EXAMPLE 16

The effect on wax selectivity of reaction temperature and catalyst concentration at constant ratio (A/B/C=1/4/1) is shown in Table VII. The procedure of Example 14, Run K, was followed except that $C_2H_4$ pressure was 7 MPa. Product purity was 99+% in all runs.

TABLE VII

| Run | A + C Pretreat [Zr]/°C./days | $Zr(OPr)_4$ Conc. mM | °C. | g. Product/ g. $Zr(OPr)_4$/ hr | % Selectivity to $C_{20+}$ Wax |
|---|---|---|---|---|---|
| V | 0.05/25/3 | 0.13 | 120 | 2,600 | 75 |
| W | 0.05/25/5 | 0.18 | 120 | 16,600 | 65 |
| X | 0.05/25/2 | 0.22 | 120 | 14,600 | 62 |
| Y | 0.05/25/3 | 0.33 | 120 | 17,600 | 60 |
| Z | 0.05/25/3 | 0.13 | 150 | 2,400 | 64 |
| AA | 0.05/25/3 | 0.33 | 150 | 7,800 | 52 |

At both 120° C. and 150° C., the selectivity to wax increased with decreasing catalyst concentration. The loss of activity at the lowest catalyst concentration was due to catalyst poisons, but in systems with lower poison levels both high activity and high selectivity to wax is obtained.

Wax selectivity increases with decreasing temperature (Run V vs Run Z, and Run Y vs Run AA). Therefore lower temperatures (higher ethylene concentrations at constant pressure) are preferred for a wax process. However, in order to maintain the high molecular weight end of the wax distribution in solution and prevent deposition on cooling surfaces, it is preferred to operate at about 100° to 180° C. and most preferably at about 120° to 150° C. Since higher temperatures are preferred because of higher rates and lower fouling, it is necessary to increase ethylene pressure to maintain high ethylene concentrations which are needed for activity, product purity and wax selectivity.

EXAMPLE 17

The effects of solvent type and temperature on the operability of a wax process are given in Table VIII. The procedure of Example 14, Run M was followed except for solvent type and temperature.

TABLE VIII

| Run[a] | Solvent | °C. | % Selectivity to $C_{20+}$ Wax | Reactor Fouling |
|---|---|---|---|---|
| BB | n-Heptane | 119 | 60 | Heavy |

TABLE VIII-continued

| Run[a] | Solvent | °C. | % Selectivity to $C_{20+}$ Wax | Reactor Fouling |
|---|---|---|---|---|
| CC | Toluene | 119 | 64 | Trace |
| DD | n-Heptane | 133 | 55 | Medium |
| EE[b] | n-Heptane | 133 | 52 | None |
| FF | i-Octane | 133 | 52 | Medium |
| GG | Methylcyclohexane | 133 | 52 | None |
| HH | Isopar G[c] | 133 | 55 | None |
| II | Toluene | 133 | 50 | None |

[a] Average of three or more batch runs made consecutively. Product was pressured from the reactor at reaction temperature and fresh solvent and catalyst were charged within minutes.
[b] 0.1 mmole hexamethylbenzene was added to the solution containing 0.1 mmole Zr(OPr)$_4$.
[c] Exxon high purity isoparaffinic solvent, bp 160–174° C.

At temperatures below about 120° C., fouling occurs in n-heptane, a poor solvent for polyethylene, whereas very little fouling occurs in toluene, a good solvent for polyethylene (Runs BB and CC). At 133° C. fouling was moderate in poor solvents (heptane and i-octane) (DD and FF) and it was absent in better solvents (methylcyclohexane. Isopar G and toluene) (GG, HH and II). When a pi-base additive was present in the catalyst, there was no fouling in heptane at 133° C. Above about 135°–140° C., there is no fouling even in the linear paraffinic solvents.

The fouling data in this example were obtained from repetitive batch runs in which incomplete drainage and decomposition of catalyst on reactor walls would favor high fouling. In a continuous unit, and particularly a tubular unit, the fouling tendencies would be substantially less than in these batch runs at the same temperatures. Thus, for best process operability, temperatures above about 120° C. are preferred. When autorefrigeration units are used, fouling is further minimized and temperatures as low as 100° C. may be used advantageously to increase selectivity to wax.

EXAMPLE 18

Various zirconium alkoxide compounds and alkyl aluminum cocatalysts may be used to make waxes under the appropriate conditions as shown in Table IX. All runs were made in 300 ml dry toluene at 7 MPa ethylene pressure.

TABLE IX

| Run | JJ | KK | LL | MM | NN |
|---|---|---|---|---|---|
| Catalyst | | | | | |
| (a) AlEt$_2$Cl, mmoles | 0.1 | 0.1 | 0.07 | 0.075 | 0.1 AtEt$_2$OBu |
| (b) AlEtCl$_2$, mmoles | 0.4 | 0.4 | 0.35 | 0.6 | 0.4 |
| (c) ZrCpd | Zr(OBu)$_4$ | Zr(OPr)$_2$(OBu$_2$) | Zr(OPr)$_3$OCH$_2$CH$_2$NMe$_2$ | Zr(OPr)$_4$ | Zr(OPr)$_4$ |
| mmoles | 0.1 | 0.1 | 0.07 | 0.075 | 0.1 |
| (d) Base | — | — | — | Pyridine | — |
| mmoles | — | — | — | 0.3[a] | — |
| (a + c) Pretreat °C./days | 25/1 | 25/1 | 25/1 | 25/1 (5.6 MPa) | 80/15 min. |
| Polymerization | | | | | |
| Temp. °C. | 120 | 150 | 120 | 120 | 120 |
| Time, min. | 30 | 15 | 30 | 15 | 30 |
| Results | | | | | |
| g/g ZrCpd/hr | 21,000 | 10,300 | 3,920 | 13,500 | 10,900 |
| % Purity | 99.4 | 99.9+ | 99.9+ | 99.9+ | 99.9+ |
| % Selectivity to $C_{20+}$ Wax | 52 | 56 | 60 | 60 | 55 |

[a] Added with the AlEtCl$_2$.

EXAMPLE 19

The procedure of Example 14, Run G, was followed except that ZrCl$_4$ was used instead of Zr(OPr)$_4$. Polymerization rate was 15,300 g/g ZrCl$_4$/hr based on a 30 minute run, the $C_{12-20}$ alpha olefin purity was 99.5% and the selectivity to $C_{20+}$ wax was 57.8%. In contrast to Zr(OR)$_4$ catalysts which require at least 3 AlEtCl$_2$ to obtain exchange between OR and Cl groups, the ZrCl$_4$ was effective with only a stoichiometric amount of AlEt$_2$Cl.

EXAMPLE 20

The effects of cocatalyst proportions on a zirconium dichloride dialkoxide catalyst are shown in Table X. The procedure of Example 17, Run DD was followed except for the catalyst, the cocatalyst ratios and the oligomerization temperatures.

Runs A and B contain no dialkyl aluminum chloride and are unsatisfactory because of low activity. However, in Run B the selectivity to $C_{20+}$ wax is acceptable because the EtAlCl$_2$/ZrCl$_2$(OR)$_2$ ratio is within the range of 0 to 3.

Run C contains no EtAlCl$_2$ and suffers from low activity although the wax selectivity is above 50% at EtAlCl/ZrCl$_2$(OR)$_2$=1.

In Run D the EtAlCl$_2$/ZrCl$_2$(OR)$_2$ ratio of 4 is too high and yields an unacceptably low wax selectivity. Runs E and F used the preferred ratios of all three components and they gave high selectivity to wax at extraordinarily high oligomerization rates. Run G at 100° C. versus Run F at 140° C. shows that high rate is maintained and product purity is increased due to higher ethylene solubility and the selectivity to wax increased.

TABLE X

| Run | Mole Ratio A/B/C[a] | Diluent (350 ml) | Oligomerization °C. | MPa | Min. | g. Product/ g. ZrCl$_2$(OPr) 2/hr. | % Purity[b] | % Selectivity to $C_{20+}$ Wax |
|---|---|---|---|---|---|---|---|---|
| A | 0/4/1 | n-Heptane | 140 | 7 | 30 | 5350 | 98.6 | 42 |
| B | 0/2/1 | " | " | " | " | 3000 | 99.6 | 70 |
| C | 1/0/1 | " | " | " | " | 4130 | 95.6 | 52 |
| D | 1/4/1 | " | " | " | " | 11600 | 96.8 | 34 |

TABLE X-continued

| Run | Mole Ratio A/B/C[a] | Diluent (350 ml) | Oligomerization °C. | MPa | Min. | g. Product/ g. ZrCl$_2$(OPr) 2/hr. | % Purity[b] | % Selectivity to C$_{20+}$ Wax |
|---|---|---|---|---|---|---|---|---|
| E | 1/2/1 | " | " | " | 20 | 30800 | 95.0 | 57 |
| F | 1/1/1 | " | " | " | 15 | 26100 | 95.3 | 61 |
| G | 1/1/1 | " | 100 | " | 30 | 27200 | 98.6 | 66 |

[a] A/B/C = Et$_2$AlCl/EtAlCl$_2$/ZrCl$_2$(OPr)$_2$
[b] Wt. % Linear alpha olefins in C$_{12-20}$ fraction

What is claimed is:

1. A process for preparing an olefinic reaction product comprising at least 50 wt. % C$_{20+}$ waxes which consists of polymerizing an ethylene containing gas in the presence of:
   (a) an aluminum alkyl compound having the formula R$_2$AlX', wherein X' is selected from the group consisting of fluorine, chlorine, bromine and iodine, and R is an alkyl, cycloalkyl or aralkyl group;
   (b) an aluminum alkyl compound having the formula RAlX$_2$, wherein X is selected from the group consisting of chlorine and bromine, and R is an alkyl, cycloalkyl or aralkyl group; and
   (c) a zirconium compound having the formula ZrX$_n$Y$_{4-n}$, wherein X is selected from the group consisting of chlorine and bromine, Y is selected from the group consisting of alkoxide, aryloxide, carboxylate, and enolate, n=0 to 4, the ratio of a/c is 1 the ratio of b/c is: 0 when n=4; 0 to 2 when n=3; 0 to 3 when n=2; 2 to 4 when n=1; and 2 to 6 when n=0, in the presence of a diluent at a reaction temperature of 100° C. to 180° C. and an ethylene pressure above 50 psig.

2. A process according to claim 1, wherein said temperature is about 120° C. to about 150° C.

3. A process according to claim 1, wherein X and X' are chlorine.

4. A process according to claims 1 or 3 wherein n=2 to 4.

5. A process according to claims 1 or 3 wherein n=2.

6. A process according to claim 1, wherein Y is an alkoxide, aryloxide or carboxylate.

7. A process according to claim 1, wherein Y is an alkoxide.

8. A process according to claim 1, wherein the product contains at least 90 mole % linear olefins of which greater than 50 wt. % are C$_{20+}$ waxes.

* * * * *